US012752123B2

(12) United States Patent
Perryman et al.

(10) Patent No.: US 12,752,123 B2
(45) Date of Patent: Oct. 6, 2026

(54) EARPIECE ASSEMBLY TO INTERACT WITH IMPLANTABLE NEURAL STIMULATORS

(71) Applicant: CURONIX LLC, Pompano Beach, FL (US)

(72) Inventors: Laura Tyler Perryman, Pompano Beach, FL (US); Chad David Andresen, Miami Beach, FL (US); Graham Patrick Greene, Miami Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 247 days.

(21) Appl. No.: 18/534,311

(22) Filed: Dec. 8, 2023

(65) Prior Publication Data

US 2024/0216699 A1 Jul. 4, 2024

Related U.S. Application Data

(63) Continuation of application No. 16/989,071, filed on Aug. 10, 2020, now Pat. No. 11,844,951, which is a
(Continued)

(51) Int. Cl.
*A61N 1/372* (2006.01)
*A61N 1/36* (2006.01)
*A61N 1/378* (2006.01)

(52) U.S. Cl.
CPC ..... *A61N 1/37229* (2013.01); *A61N 1/36075* (2013.01); *A61N 1/36128* (2013.01); *A61N 1/3787* (2013.01)

(58) Field of Classification Search
CPC ........................ A61N 1/37229; A61N 1/36075
(Continued)

(56) References Cited

U.S. PATENT DOCUMENTS 10,737,098 B2 8/2020 Perryman et al.
2007/0213783 A1 9/2007 Pless
(Continued)

FOREIGN PATENT DOCUMENTS

WO 2012103519 A2 8/2012
WO 2012138782 A1 10/2012
(Continued)

OTHER PUBLICATIONS

U.S. Appl. No. 62/098,946, filed Dec. 31, 2014.
(Continued)

*Primary Examiner* — Nicole F Johnson
(74) *Attorney, Agent, or Firm* — Sanders IP Law

(57) ABSTRACT

An ear-piece assembly includes (i) an antenna portion enclosing a transmitting antenna configured to send one or more input signals containing electrical energy to a passive implantable neural stimulator device such that the passive implantable neural stimulator generates one or more stimulation pulses suitable for stimulating a neural structure in the craniofacial region solely using the electrical energy in the input signals; and (ii) an enclosure coupled to the antenna portion, wherein enclosure is sized and shaped to be mounted on a helix portion of an ear such that, when worn by a patient, weight from the enclosure is distributed over the helix portion of the ear for the enclosure to rest thereon, wherein the enclosure comprises (i) a controller module configured to provide the one or more input signals to the transmitting antenna, and (ii) a battery adapted to provide energy to the ear-piece assembly.

20 Claims, 14 Drawing Sheets

Related U.S. Application Data continuation of application No. 15/738,903, filed as application No. PCT/US2016/038747 on Jun. 22, 2016, now Pat. No. 10,737,098.

(60) Provisional application No. 62/182,833, filed on Jun. 22, 2015.

(58) Field of Classification Search
USPC .......................................................... 607/46
See application file for complete search history.

(56) References Cited

U.S. PATENT DOCUMENTS

| | | | | |
|---|---|---|---|---|
| 2008/0085024 | A1 | 4/2008 | Linkenkaer-Hansen | |
| 2011/0166619 | A1* | 7/2011 | de Vos ................. | A61N 1/3601 607/42 |
| 2011/0172733 | A1 | 7/2011 | Lima et al. | |
| 2013/0310901 | A1* | 11/2013 | Perryman .............. | A61N 1/025 607/117 |
| 2014/0058480 | A1 | 2/2014 | Perryman et al. | |
| 2014/0249608 | A1 | 9/2014 | Rogers | |
| 2014/0330336 | A1 | 11/2014 | Errico et al. | |
| 2014/0350640 | A1 | 11/2014 | Patrick et al. | |
| 2018/0178020 | A1 | 6/2018 | Perryman et al. | |

FOREIGN PATENT DOCUMENTS

| | | | |
|---|---|---|---|
| WO | 2013019757 | A2 | 2/2013 |
| WO | 2013025632 | A1 | 2/2013 |
| WO | 2013040549 | A1 | 3/2013 |

OTHER PUBLICATIONS

Authorized Office Lee W. Young, International Search Report and Written Opinion in PCT/US2016/038747 mailed Sep. 1, 2016, 10 pages.

PCT International Preliminary Report on Patentability in International Application No. PCT/US2016/038747, dated Dec. 26, 2017, 5 pages.

* cited by examiner

EARPIECE ASSEMBLY TO INTERACT WITH IMPLANTABLE NEURAL STIMULATORS

CROSS-REFERENCE TO RELATED APPLICATIONS

This application is a continuation of U.S. application Ser. No. 15/738,903, filed Dec. 21, 2017, now allowed, which is a 371 of PCT/US16/38747, filed Jun. 22, 2016, which claims the benefit of U.S. Provisional Application No. 62/182,833, filed on Jun. 22, 2015. The complete disclosures of all of the above patent applications are hereby incorporated by reference in their entirety for all purposes.

TECHNICAL FIELD

This application relates generally to a transmitter for interacting with implantable neural stimulators.

BACKGROUND

Craniofacial implants may treat neuropathy such as craniofacial pain, cluster headaches, and migraines.

SUMMARY

In one aspect, some implementations provide an ear-piece assembly that includes an antenna portion enclosing a transmitting antenna configured to send one or more input signals containing electrical energy to a passive implantable neural stimulator device such that the passive implantable neural stimulator generates one or more stimulation pulses suitable for stimulating a neural structure in the craniofacial region solely using the electrical energy in the input signals; an enclosure coupled to the antenna portion, wherein enclosure is sized and shaped to be mounted on the helix portion of an ear such that, when worn by a patient, weight from the enclosure is distributed over the helix portion of the ear for the enclosure to rest thereon, wherein the assembly comprises (i) a controller module configured to provide the one or more input signals to the transmitting antenna, and (ii) a battery adapted to provide energy to the ear-piece assembly.

Implementations may include one or more of the following features.

The enclosure may include a securing feature to stabilize the enclosure to the ear while the enclosure rests on the helix portion of the ear. The securing feature may include a plug adapted to stabilize the enclosure to the ear's anterior notch. The securing feature may include a hook adapted to anchor the enclosure to the ear's cavum conchae.

The battery may provide an operating current of at least 250 mAh when the controller module wirelessly powers the passive implantable neural stimulator device.

The controller module may include a controller interface configured for the patient to adjust a power level at which the input signal is being transmitted to the passive implantable neural stimulator. The controller interface may be placed posteriorly relative to the ear such that a force pressing into the controller interface is not going into the patient's head. The controller interface may include at least status indicator that reveals an operation status of the ear-piece assembly. The controller interface may include at least a charge/program port. The at least charge/program port may be located in a caudal aspect of the ear-piece assembly.

The transmitting antenna, in some implementations, may include a bowtie antenna configuration. The transmitting antenna may be a dipole antenna that non-inductively couples to an antenna on the passive implantable neural stimulator. The transmitting antenna may couple to the embedded antenna within the passive implantable neural stimulator which has been implanted in tissue. In some implementations, the transmitting antenna may couple to the antenna on the passive implantable neural stimulator implanted such that the electrodes create an electrical field that target the occipital nerve bundles of the patient. In some implementations, the transmitting antenna may couple to the antenna on the passive implantable neural stimulator implanted such that the electrodes create an electrical field that target the supraorbital trigeminal nerve branch.

Various implementations may be inherently low in cost compared to existing implantable neural modulation systems, and this may lead to wider adoption of neural modulation therapy for patients in need as well as reduction in overall cost to the healthcare system.

The details of one or more implementations are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
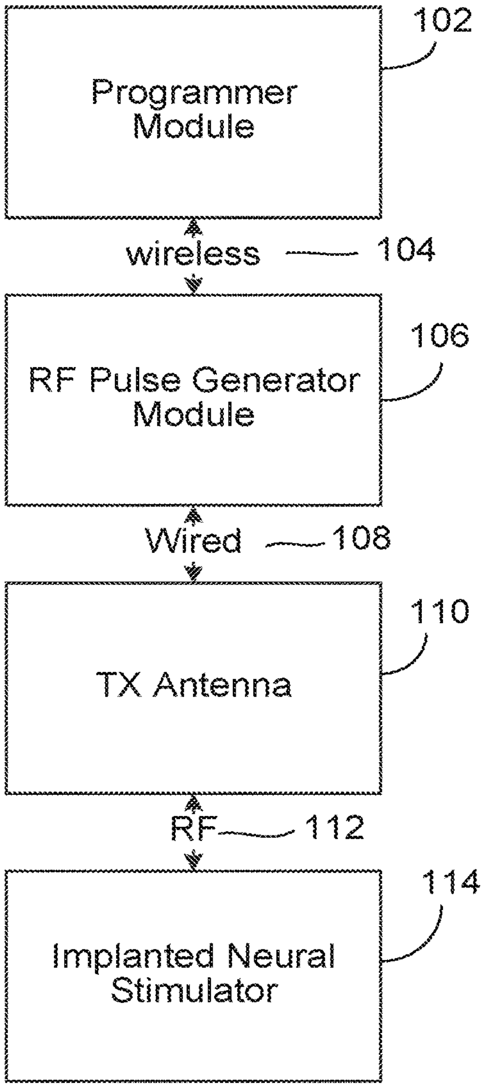
FIG. 1 depicts a high-level diagram of an example of a wireless stimulation system.

Various implementations include systems and methods for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In some instances, craniofacial neural stimulators may be implanted to treat cranial neuropathy, such as craniofacial pain, cluster headaches, and migraines. In particular, a controller device can wirelessly send input signals containing electrical energy to a passive implanted wireless stimulator device, without cable coupling or inductive coupling. The passive wireless stimulator device may target a craniofacial neural structure by applying stimulation pulses created solely using the electrical energy in the input signal received from the controller device. The passive neural stimulator device may include one or more electrodes and one or more conductive antennas (for example, dipole or patch antennas), and internal circuitry for frequency waveform and electrical energy rectification.

In various implementations, the passive neural stimulator device is powered wirelessly (and therefore does not require a wired connection) and contains the circuitry necessary to receive the pulse instructions from a source external to the body. For example, various embodiments employ internal dipole (or other) antenna configuration(s) to receive radio-frequency (RF) power through electrical radiative coupling. This allows such devices to produce electrical currents capable of stimulating nerve bundles without a physical connection to an implantable pulse generator (IPG) or use of an inductive coil.

Some implementations of the wireless stimulation system may include an ear-piece assembly for the patient to wear on his/her ear. The ear-piece controller device may include (i) an antenna structure for transmitting input signals containing electrical energy to power a passive neural stimulator device, (ii) a microwave field stimulator programmable to provide the input signals, (iii) a controller interface to allow a patient to set and adjust stimulation parameters, and (iv) a battery pack for supplying electrical power to the assembly. In more detail, the antenna structure may include an antenna housed in an overmold material for comfort when worn by the patient. The arrangement of the overmold material may also allow for flexibility and hermeticity of the encapsulated antenna and components from ingress damage. For example, the overmold material covers the antenna and protects the ventral aspect of ear-piece assembly. The ear-piece may also include an anchoring feature to secure the ear-piece assembly into, for example, the ear canal. The ear-piece assembly is generally ambidextrous, that is, it is wearable on the right or left ear.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna (s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
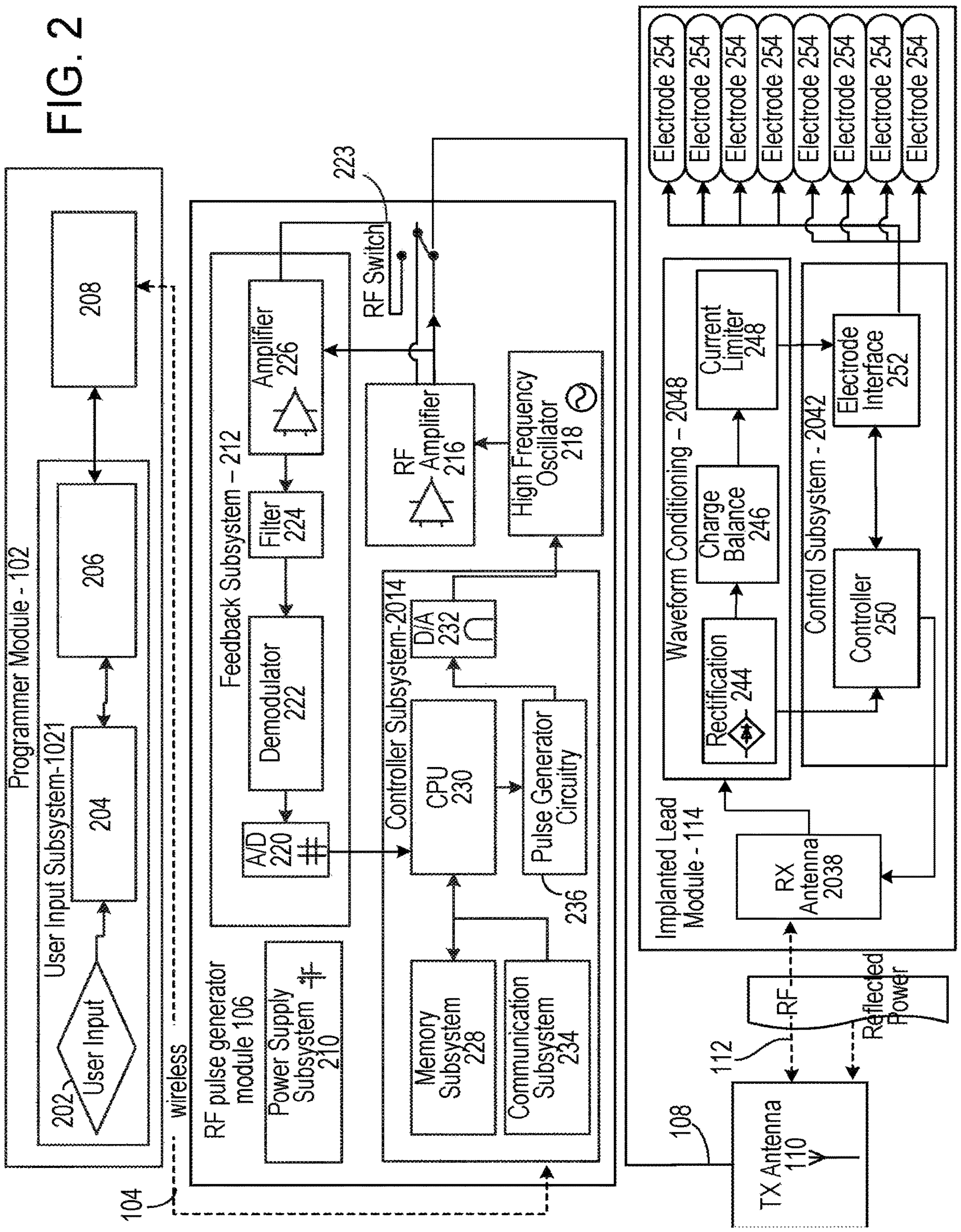
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
|---|---|
| Pulse Amplitude: | 0 to 20 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a central processing unit (CPU) 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way, the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3:
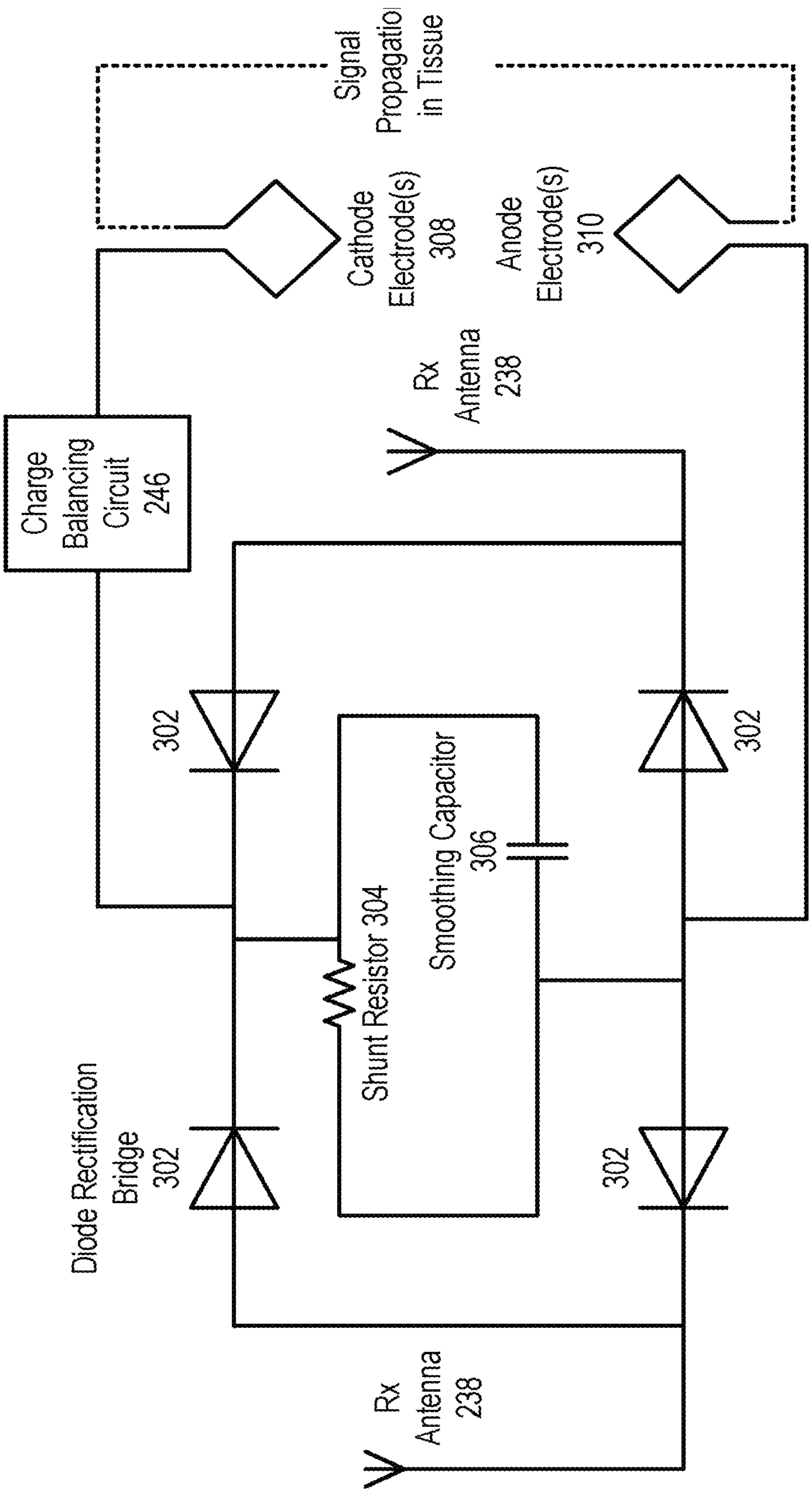
FIG. 3 is a circuit diagram showing an example of a wireless implantable stimulator device.

FIG. 3 is a circuit diagram showing an example of a wireless stimulator device 114. This example contains paired electrodes, comprising cathode electrode(s) 308 and anode electrode(s) 310, as shown. When energized, the charged electrodes create a volume conduction field of current density within the tissue. In this implementation, the wireless energy is received through a dipole antenna(s) 238. At least four diodes are connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may cause a low threshold voltage. In this implementation, a zero biased diode rectifier results in a low output impedance for the device. A resistor 304 and a smoothing capacitor 306 are placed across the output nodes of the bridge rectifier to discharge the electrodes to the ground of the bridge anode. The rectification bridge 302 includes two branches of diode pairs connecting an anode-to-anode and then cathode to cathode. The electrodes 308 and 310 are connected to the output of the charge balancing circuit 246.

Figure 4:
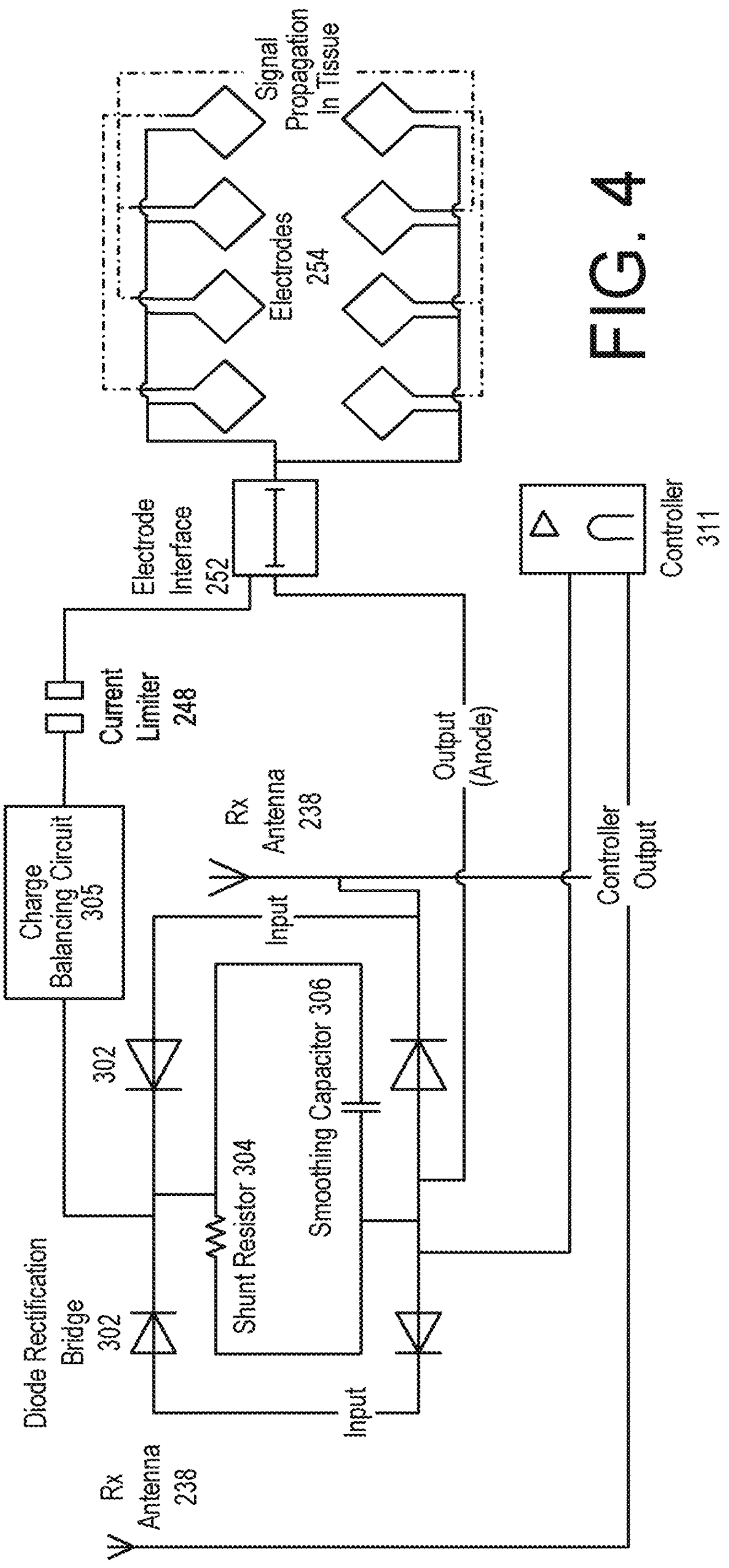
FIG. 4 is a circuit diagram of another example of a wireless implantable stimulator device.

FIG. 4 is a circuit diagram of another example of a wireless stimulator device 114. The example shown in FIG. 4 includes multiple electrode control and may employ full closed loop control. The wireless stimulation device includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may cause a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 may include two branches of diode pairs connecting an anode-to-anode and then cathode to cathode. The electrode polarity outputs, both cathode 408 and anode 410 are connected to the outputs formed by the bridge connection. Charge balancing circuitry 246 and current limiting circuitry 248 are placed in series with the outputs.

Some methods include implantation of a wireless neural stimulator device to treat conditions such as angina pain or craniofacial pain or occipital pain. Electrodes in some embodiments, may be positioned near targeted nerves in very specific regions, such as the parasternal regions on the chest, where patients usually experience angina. These methods include placement of devices under ultrasound guidance and may be performed as part of an outpatient procedure and may only use local anesthesia. The implanted wireless stimulator device does not include a power supply, such as a battery, and is powered remotely by, for example, electromagnetic energy radiated from a microwave field stimulator (MFS). The lack of an independent power source on the implanted wireless stimulator may enable a compact form factor, which is highly conducive to subcutaneous implantation. As such, the implantation method does not include implanting an implantable pulse generator (IPG). Nor does the implantation method including embedding wires that connects the stimulator device to an external power source. Compared to implantation in the epidural space for spinal cord stimulation, implantation at the targeted peripheral nerves does not require special training of the physician. Moreover, such peripheral nerve implantations may not necessitate the withholding of anti-platelet therapy and anticoagulants, something typically administered to patients with angina pain. Generally, placement of the wireless neural stimulator device is less invasive than, for example, implantation in the epidural space of the spinal cord. As such, peripheral nerve placement carries less risk of serious complications, as positioning and securing of electrodes easier compared with epidural placement. Below, examples of peripheral implantation are described in the context of treating angina, craniofacial pain, and occipital pain.

Some implementations may include a compact ear-piece assembly housed in one package that includes (i) an antenna portion for transmitting input signals containing electrical energy to power a passive neural stimulator, (ii) a microwave field stimulator programmable to provide the input signals, (iii) a controller interface to allow a patient to set and adjust stimulation parameters, and (iv) a battery pack for supplying electrical power to the assembly. This package, when worn by a patient on his/her ear, is full-service and capable of single-handedly interfacing with a passive neural stimulator to provide electrical energy and waveform stimulation parameters such that the passive neural stimulator can stimulate neural structures in the craniofacial region solely using the electrical energy received wirelessly from the ear-piece assembly.

Figure 5A:
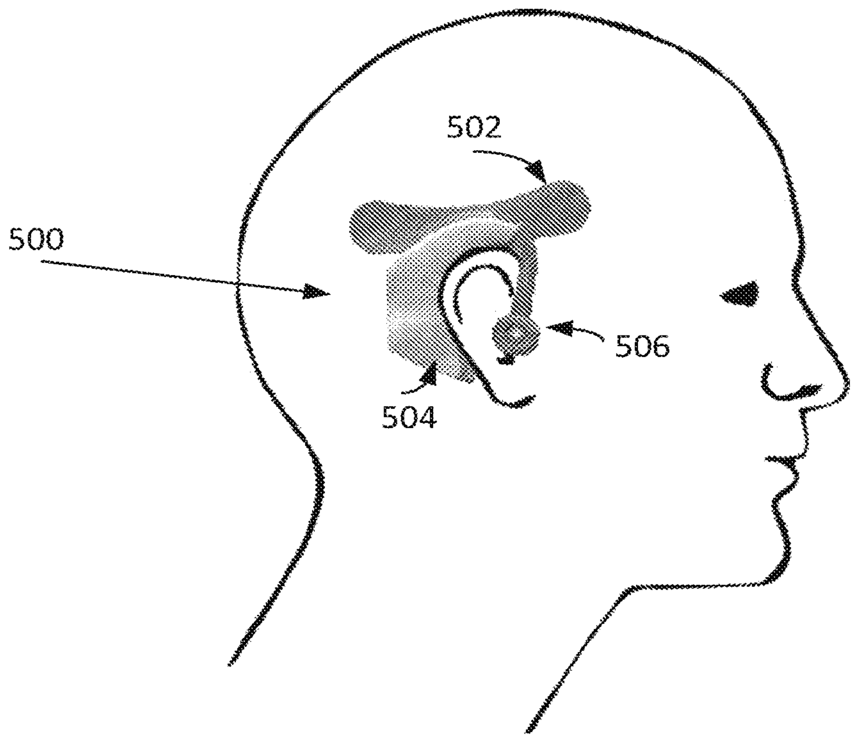
FIG. 5A is a lateral view of an example of an earpiece assembly placed onto a person's ear.

FIG. 5A is a lateral view of an example of an earpiece assembly 500 placed secured onto a person's ear. Ear-piece assembly 500 includes an antenna portion 502, an enclosure 504, and may include securing element 506. Generally, ear-piece assembly 500 is arranged and packed such that the majority of the weight is applied toward the antihelix of the ear rather than posterior. Ear-piece assembly 500 is shaped to resemble a 90° rotated pyramid with the base of the pyramid located closer to the ear such that the torque force resulting from weight lateral of the resting point on the ear is substantially reduced.

Antenna portion 502 includes a bowtie antenna encapsulated inside an overmold material. Example materials for the overmold may include polyurethane, polyethylene, acrylonitrile butadiene styrene (ABS), or polycarbonate. Such overmold materials are applied to render the wearable stimulation device comfortable and flexible for the patient recipient. The overmold material may also provide long-term protection and aesthetic values. The antenna is electrically matched to tissue and thus can "see" past the overmold materials in the sense of being able to transmit electromagnetic signals beyond the overmold material without having reflection before the EM wave hits tissue.

Figure 5B:
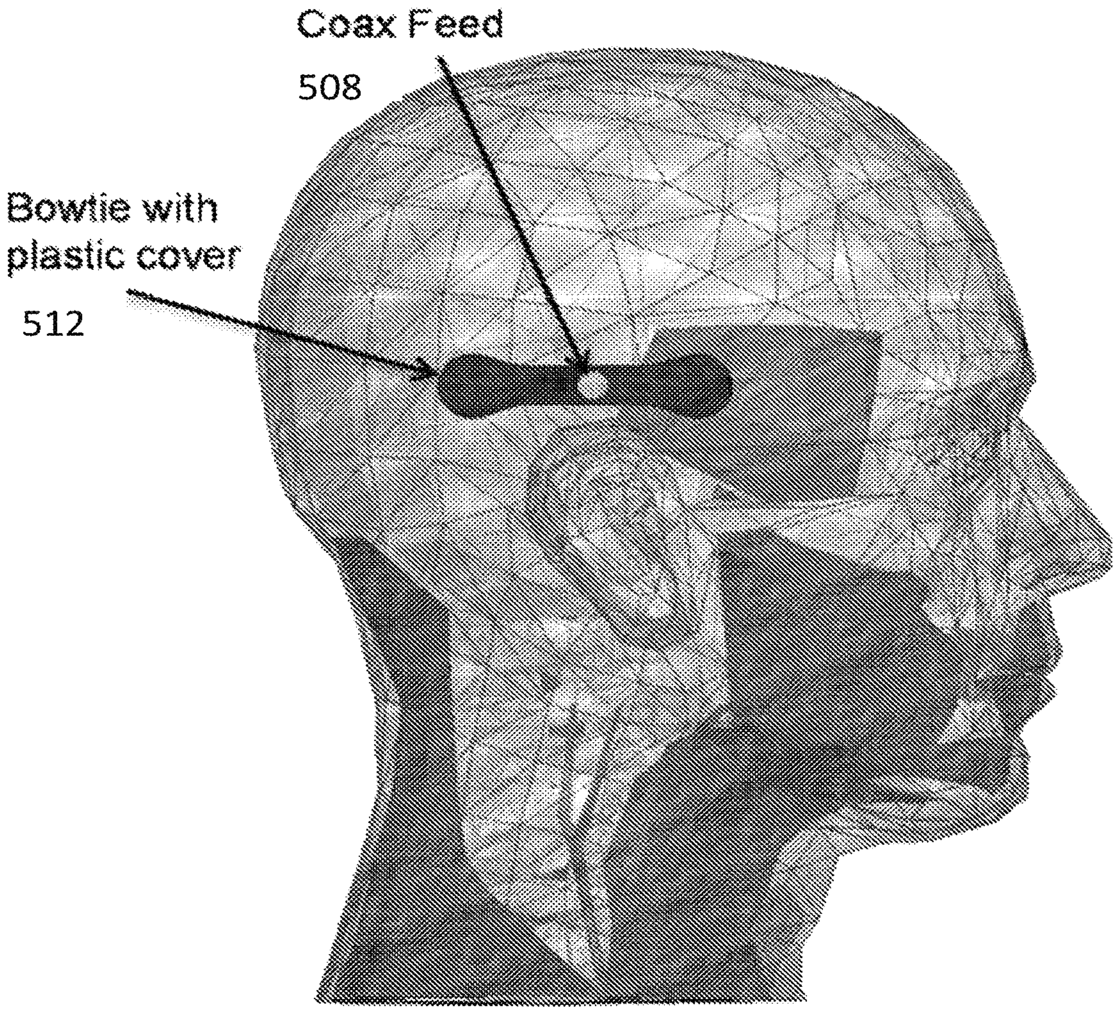
FIG. 5B highlights a lateral view of an example of a bowtie antenna configuration in the example of FIG. 5A.

The antenna inside the overmold material may be a bowtie configuration 512, as shown in FIG. 5B. The bowtie antenna configuration 512 includes a coax feed 508 for a coax connection to a controller device such as a microwave field stimulator (MFS) housed in the ear-piece assembly 500. The coax feed generally assumes a 50Ω load. The bowtie antenna configuration 512, as placed above the ear, radiates electromagnetic (EM) energy through the skin and into a receiving antenna implanted subcutaneously under the skin. Bowtie antenna configuration 512 may generally include a signal metal layer, a ground metalplane, and dielectric layers. Further details of the bowtie antenna configuration 512 can be found in U.S. Provisional Application No. 62/098,946, the entire contents of which are incorporated herein by reference.

Referring to FIGS. 7A-7B and 8A-8C, the bowtie antenna configuration 512 includes two leaves, namely 512A and 512B, each of which has a width W of, for example, 20 mm. The combined length L of leaves 512A and 512B may be, for example, 85 mm. The two leaves 512A and 512B may form an angle of D. Here, the bowtie antenna configuration 512 functions like a dipole transmitting antenna and the geometrical parameters of L, W, and D can determine the resonance behavior of bowtie antenna configuration 512. Leaves 512A and 512B may include rounded fillets with a radius of, for example, 10 mm. The rounded fillets may reduce high concentration of electromagnetic field in the corners and contribute to a more uniform radiation pattern than sharp fillets without rounded fillets. Further, the two leaves 512A and 512B converge at feed port 508 where a 50Ω feed port can be located. The feed port 508 may connect bowtie antenna configuration 512 to, for example, a microwave field stimulator (MFS) device. By way of example, BNC (Bonet Neill-Concelman) or SMC (SubMiniature version A) type connectors can be used to connect 50Ω feed port to an MFS device 902 through a co-axial cable The bowtie antenna length can vary between, for example, 0.1 mm and 5 cm. The operation of the bowtie antenna configuration 512 may induce a specific absorption rate (SAR) inside the skull of the patient. In some implementations, operational SAR may be limited to less than 4 W/kg. Bowtie antenna configuration 512 enclosed in the overmold material may be shaped to match the side of the head without contacting with the skin. This arrangement may allow the thin antenna of the two leaves 512A and 512B to sit comfortably from 1 mm to 2 cm away from the side of the head.

Referring to FIGS. 5A, 7A-7C, and 8A-8C, ear-piece assembly 500 may further include enclosure 504, which houses a battery 802 and a controller module 804. Battery 802 may have a dimension of, for example, 22 mm by 31 mm. Battery 802 may, for example, offer operating current at 250-400 mAh, and last at least 8 hours. Controller module 804 may include, for example, a microwave field stimulator (MFS), such as the RF pulse generator module 106 of FIG. 2. Controller module 804 may be electrically coupled to bowtie antenna configuration 512 such that controller module 804 provides input signals to bowtie antenna configuration 512 and bowtie antenna configuration 512 transmits such input signals containing electrical energy and stimulation waveform parameters to a passive neural stimulator. The co-axial cable may run though hinge point 806, which may also provide a mechanic pivoting point such that the relative orientation of antenna portion 502 can be adjusted. Controller module 804 may be packaged as heavier PCB assembly components. These components could be distributed as close to the ear as possible. As illustrated, the shape of the enclosure 504 tapers posteriorly to the controller interface 520. This tapering helps in weight distribution and aids the user in finding the panel while the unit is still on the user's head.

In particular, FIG. 5A illustrates an ear-piece assembly 500 to be worn on the right side of the patient which FIGS. 7A-7C, and 8A-8C showcase ear-piece assembly 500 to be worn on the left side of the patient. As illustrated in FIGS. 7A-7C, and 8A-8C, enclosure 504 includes a left cover 504A that is exterior (i.e., facing away from the patient) in this left-side configuration. Enclosure 504 also includes a right cover 504A that is interior (i.e. facing towards the patient's skull) in this left-side configuration. Enclosure 504 further includes a bend cover 504C that matches the helical curvature on the back side of the auricle where ear piece assembly 500 is to be mounted for operation. Enclosure 504 may further include securing element 506 extending from bend cover 504C. Bend cover 504C and securing element 506 generally facilitates anchoring ear-piece assembly 500 in place. Bend cover 504C may pivot securing feature 506 up and down. This pivoting capability may accommodate differences in ear shapes of different individuals. The shape of ear may refer to the distance from the ear's top point, the helix, to the anterior notch. Securing element 506 may include a dome plug adapted to be inserted into the ear's cavum conchae to secure ear-piece assembly 500 in place. Securing element 506 may also include an anchoring feature such as a hook that can be secured into the anterior notch of the auricle. Securing feature 506 can be made of a soft rubber (e.g., urethane, or silicone) when a plug is used or a smooth finished hard plastic when a hook is used. Ear piece assembly 500 may be ambidextrous, so that the same device can be used on either the left or right side of the head. Only the in-ear hook or plug may need to be flipped (i.e. popped out and then placed on the opposite side) to accommodate the alternate side of the head. In some instances, enclosure 504 includes a mating feature to attach the anchor plug or dome to ear-piece assembly 500.

Enclosure 504 may further include controller interface 520 on the back side of enclosure 504. Referring to FIGS. 6A, 7B-7C, and 8A-8C, controller interface 520 may include power-on button 522 to turn on the ear-piece assembly 500, power indicator 523 that indicates whether ear-piece assembly 500 is powered on, adjustment buttons 524A and 524B to notch up or down the power level at which the input signal is being transmitted to a passive neural stimulator assembly device. As illustrated, controller interface 520 is generally planar and parallel to the height of the patient. Controller interface 520 is visible and is placed onto the posterior aspect so that the force of pressing the buttons is not going into the head. Controller interface 520 may include one to six buttons to configure settings. Controller interface 520 may include one to ten LED lights to convey operation status. Controller interface 520 may further include a charger/programmer port 526 to accommodate a cable, for example, a Universal Serial Bus (USB) or firewire 1394 cable. An operator, such as the patient or a clinician, may recharge ear-piece assembly 500 or adjust settings, such as the power level or the stimulation waveform parameter being transmitted to the passive neural stimulator, by using this cable to connect ear-piece assembly. The charger/programming port 526 is also located on the caudal aspect of earpiece assembly 400. This location enhances the aesthetic appeal by discreetly hiding the charger/programming port 526.

Figure 6A:
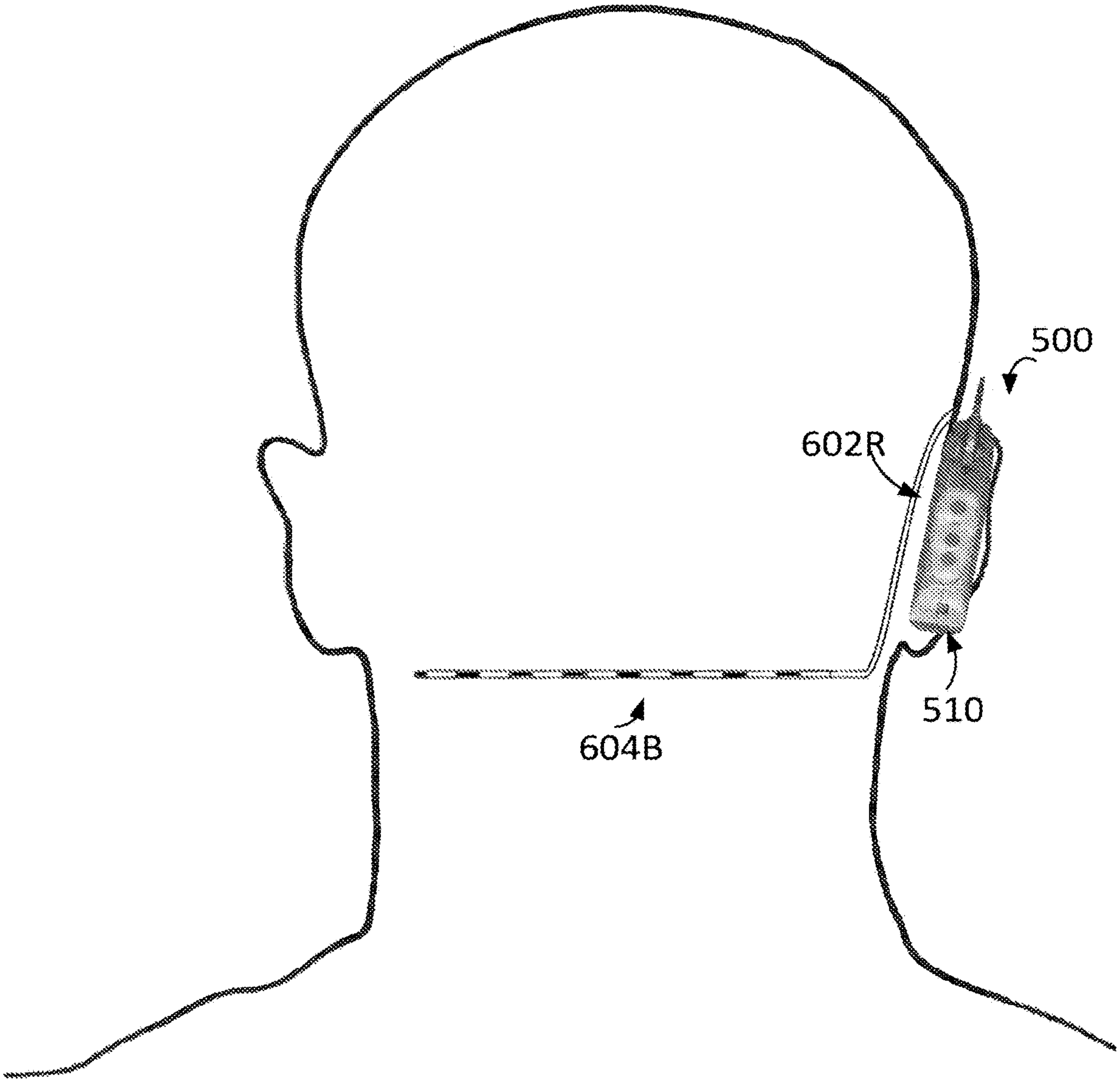
FIG. 6A is a posterior view of the example of the earpiece assembly of FIG. 5A.
Figure 6B:
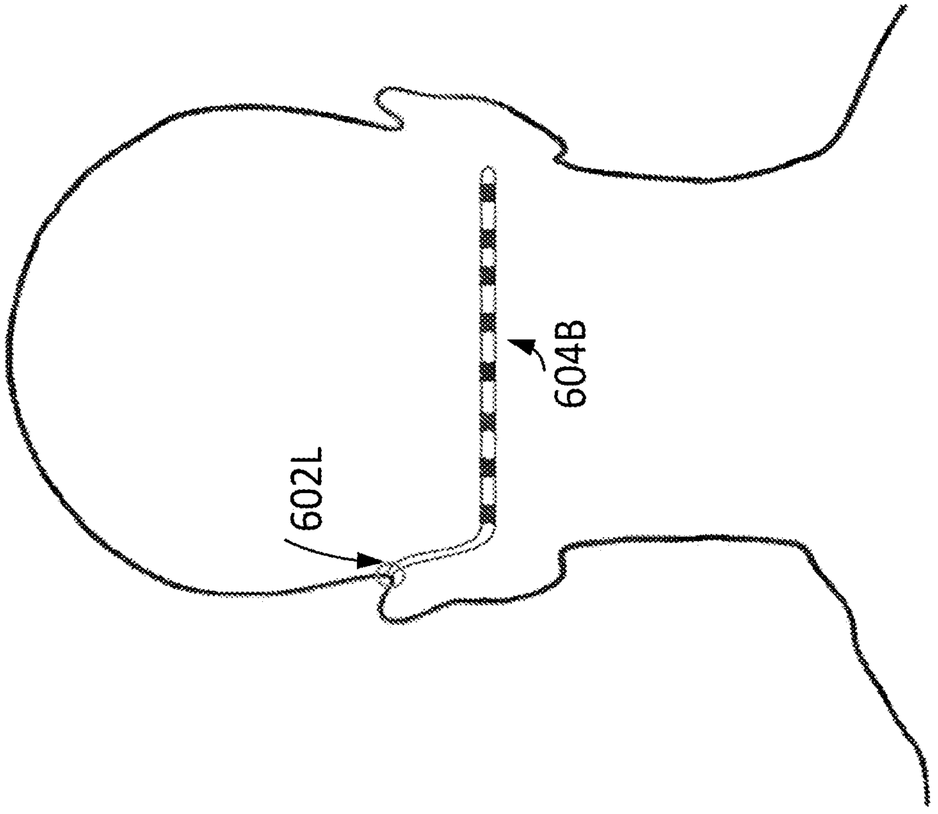
FIG. 6B-6C show examples of subcutaneously placed passive neural stimulator devices.
Figure 6C:
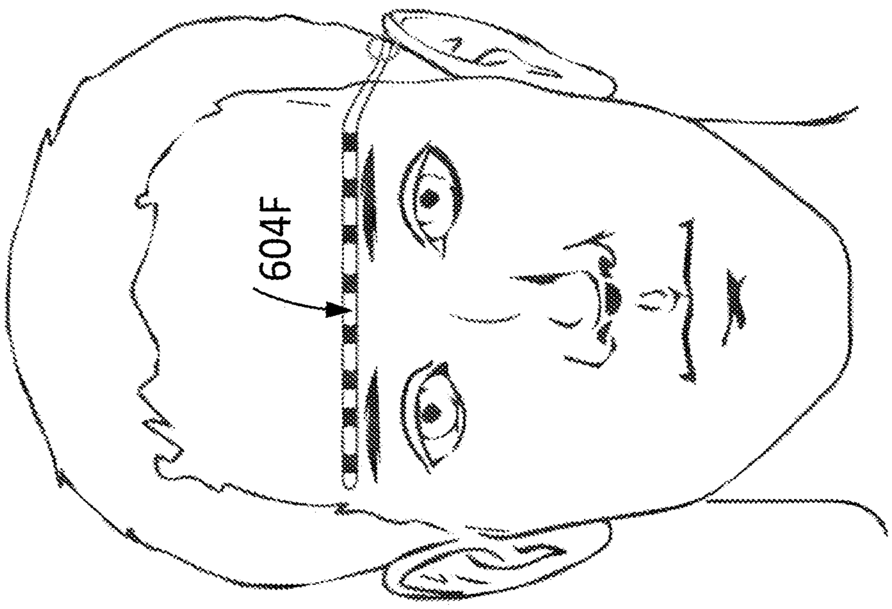
Figure 7A:
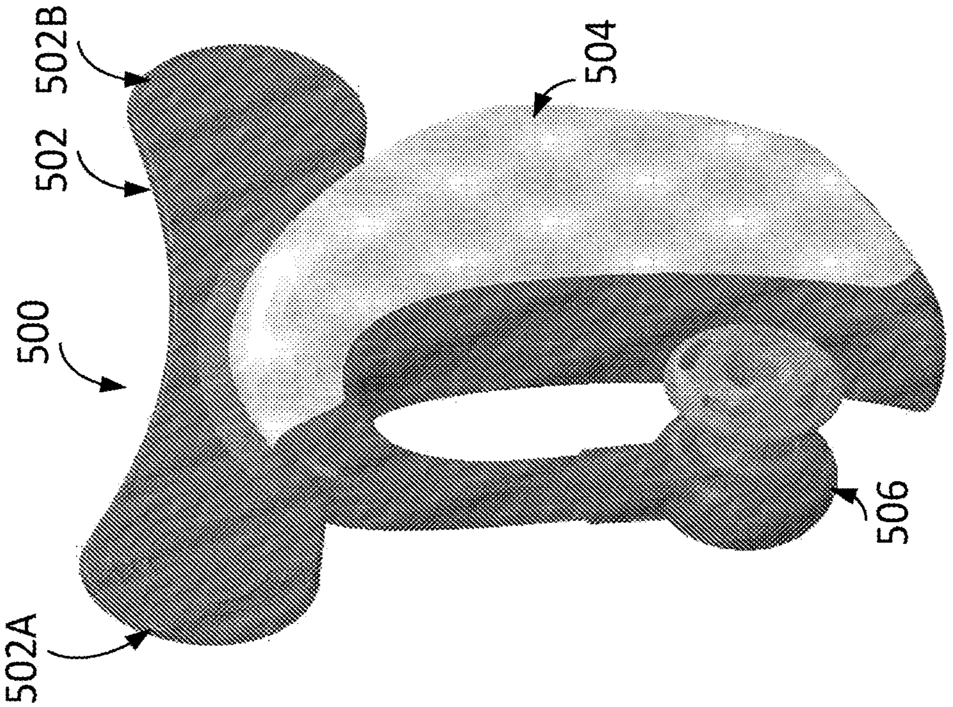
FIGS. 7A-7C are perspective views of the example of the earpiece assembly of FIG. 5A.
Figure 7B:
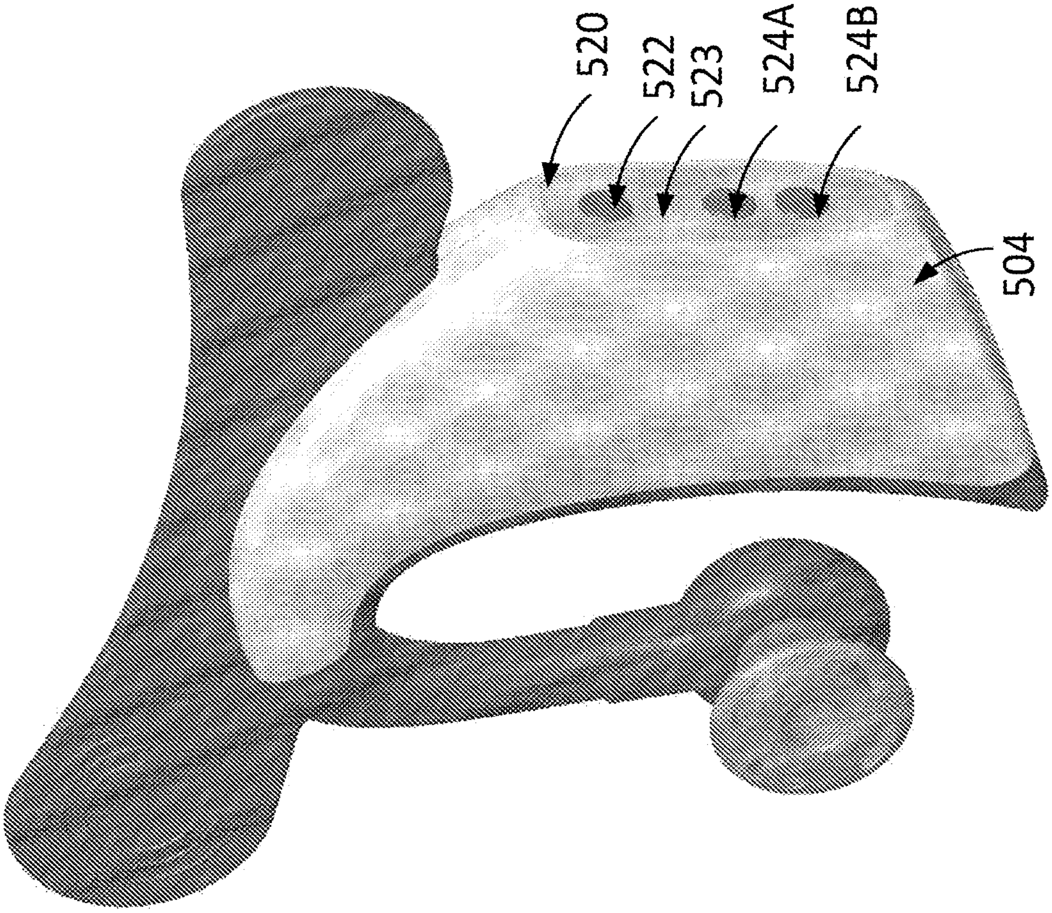
Figure 7C:
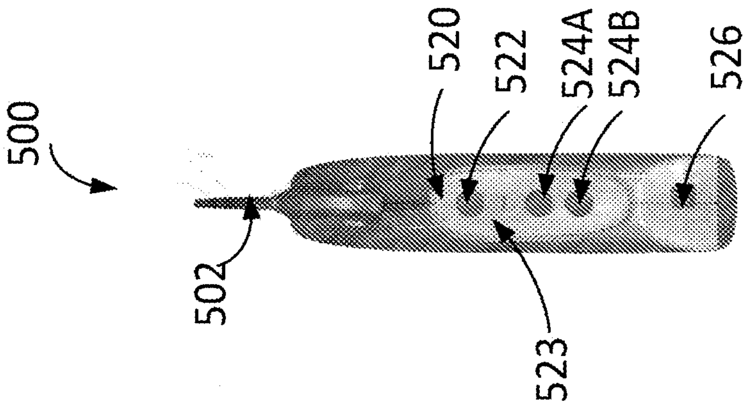
Figure 8A:
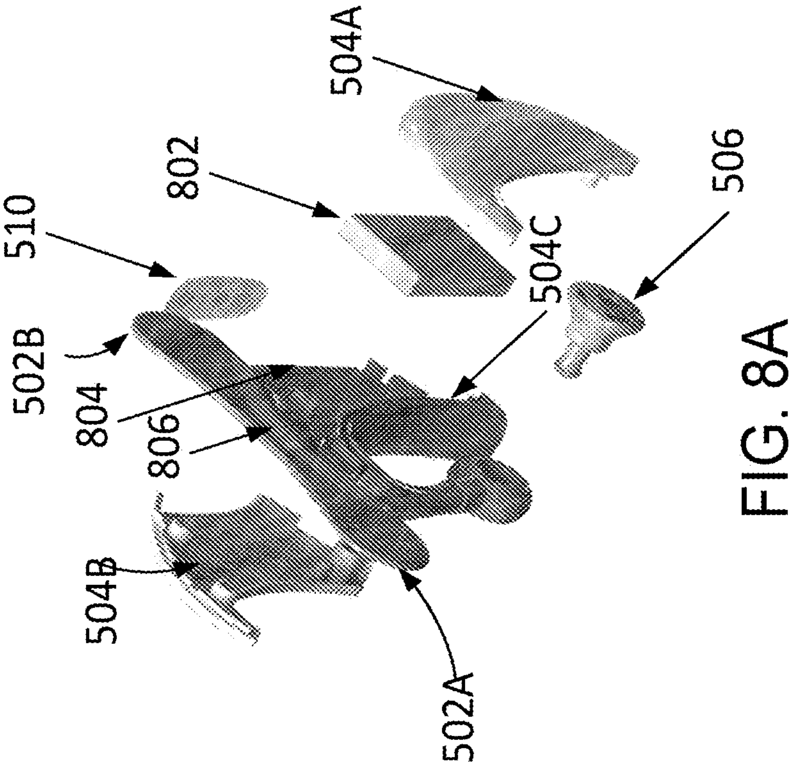
FIG. 8A-8C are exploded views of the example of the earpiece assembly of FIG. 5A.
Figure 8B:
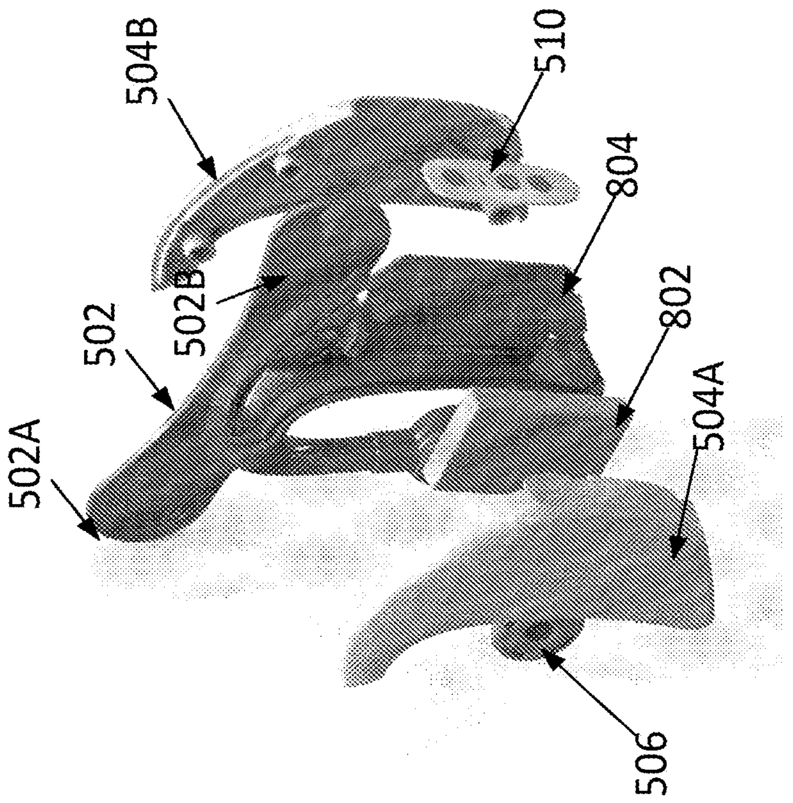
Figure 8C:
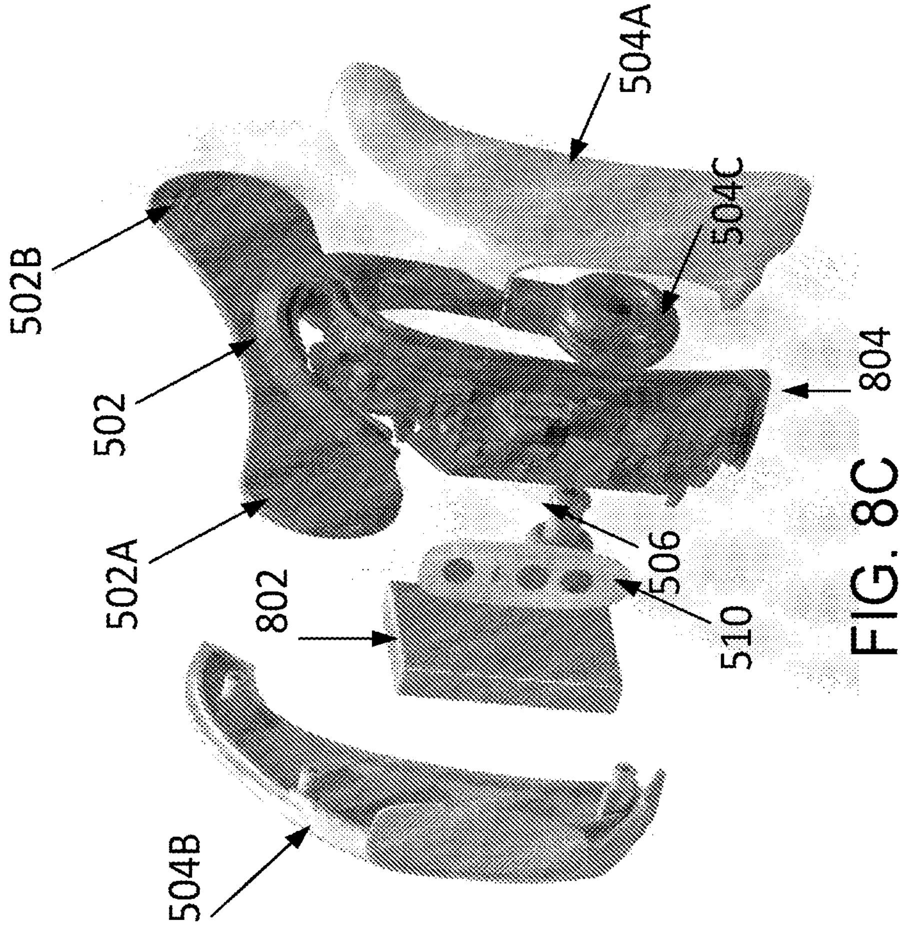

FIGS. 6B-6C illustrate examples of wireless neural stimulator devices 601 and 602 subcutaneously implanted to treat craniofacial pain and occipital pain. In particular, implantation of wireless neural stimulator devices 601 and 602 can utilize a common incision port, for example, entry point 603 above the left ear lobe. As illustrated below, wireless neural stimulator devices 601 and 602 can be implanted one at a time using the same assembly of introducer and needle style through entry point 603.

FIG. 6B depicts lateral a wireless neural stimulator device 601 subcutaneous placed across the posterior cranium above the occipital crest to target the occipital nerve bundles, via entry point 603 above the left ear lobe. In this example, a treating physician makes a surgical incision (for example, less than 2 mm) at entry point 603 above the left ear of the patient. The incision point generally avoids the facial area to avoid leaving observable scar marks. In one example, surgical incision may be made by using a scalpel and under local anesthesia. Next, a combination of an introducer and a needle stylet may be inserted through surgical incision underneath the patient's skin and in a downward motion. Thereafter, wireless neural stimulator device may be inserted through the proximal end of needle stylet. When the wireless stimulator device reaches the level just above the occipital crest, an internal stylet (such as rounded corner) may be utilized by the treating physician in a finger holding motion to lead the stimulator device to turn in the subcutaneous space and then to follow a horizontal path in the direction of the right ear. As illustrated, the stimulator device is advanced into the space of posterior cranium. Once the wireless neural stimulator device has been implanted to target the occipital nerve bundles, introducer and needle stylet can be withdrawn from surgical incision, for example, by using tearaway handles. Subsequently, wireless neural stimulator device 601 may be anchored. In this example, entry point 603 is not sealed.

FIG. 6C depicts lateral placement of wireless stimulator across the supraorbital aspect to target the supraorbital trigeminal nerve branch using the same entry point 603 above the left ear. In this example, a treating physician can insert a combination of an introducer and a needle stylet through the same entry point 603 underneath the patient's skin and in a horizontal manner and in the direction of the forehead. Thereafter, wireless neural stimulator device may be inserted through the proximal end of needle stylet and into the space of anterior cranium above the eyebrows. Once the wireless neural stimulator device has been implanted to target the supraorbital trigeminal nerve branch, introducer and needle stylet can be withdrawn from entry point 603, wireless neural stimulator device 602 may be anchored and incision at entry point 603 may be sealed. Thereafter, ear-piece assembly 500 can be mounted above the left ear to power wireless neural stimulator devices 601 and 602 by using a single antenna to radiate electromagnetic energy to both wireless neural stimulator devices.

A number of implementations have been described. Nevertheless, it will be understood that various modifications may be made. Accordingly, other implementations are within the scope of the following claims.

What is claimed is:

1. An implantable stimulator controller configured to be worn by a patient, the implantable stimulator controller comprising:
   - an antenna configured to transmit one or more signals to a passive implantable neural stimulator device via electrical radiative coupling and without inductive coupling such that the passive implantable neural stimulator device generates one or more stimulation pulses suitable for stimulating a neural structure in a craniofacial region of a patient using electrical energy in the one or more signals;
   - a controller circuit electrically coupled to the antenna and configured to generate the one or more signals and provide the one or more signals to the antenna; and
   - an enclosure that houses the controller circuit, the enclosure configured to be mounted on an ear of the patient.

2. The implantable stimulator controller of claim 1, wherein the enclosure is configured such that weight from the enclosure is distributed over a helix portion of the ear of the patient.

3. The implantable stimulator controller of claim 1, wherein the enclosure is shaped to resemble a pyramid with a base of the pyramid located closer to the ear than other portions of the pyramid.

4. The implantable stimulator controller of claim 1, further comprising a battery electrically coupled to the controller circuit and housed within the enclosure.

5. The implantable stimulator controller of claim 1, wherein the enclosure further comprises:
   - a first portion configured to engage with a backside of the ear; and
   - a second portion configured to engage with a frontside of the ear.

6. The implantable stimulator controller of claim 5, wherein the second portion includes a plug adapted to be inserted into a cavum concha of the ear.

7. The implantable stimulator controller of claim 6, wherein a position of the plug is adjustable in a direction between a top point of the ear and an anterior notch of the ear.

8. The implantable stimulator controller of claim 1, wherein the antenna is adjustably coupled to the enclosure to allow for adjustment of a position of the antenna with respect to the enclosure.

9. The implantable stimulator controller of claim 1, wherein the antenna is coupled to the enclosure and positioned such that when the enclosure is mounted on the ear of the patient the antenna is located above the ear of the patient.

10. The implantable stimulator controller of claim 1, wherein the antenna includes a dipole or a bowtie configuration.

11. A system comprising:

an implantable stimulator device configured for placement inside a craniofacial region of a patient, the implantable stimulator device configured to:

obtain one or more radiated signals; and generate one or more stimulation pulses suitable for stimulating a neural structure in the craniofacial region of the patient using electrical energy from the one or more radiated signals;

an antenna configured to transmit the one or more radiated signals to the implantable stimulator device via electrical radiative coupling and without inductive coupling;

a controller circuit electrically coupled to the antenna and configured to generate the one or more radiated signals and provide the one or more radiated signals to the antenna; and an enclosure that houses the controller circuit, the enclosure configured to be mounted on an ear of the patient.

12. The system of claim 11, wherein the enclosure is configured such that weight from the enclosure is distributed over a helix portion of the ear of the patient.

13. The system of claim 11, wherein the enclosure is shaped to resemble a pyramid with a base of the pyramid located closer to the ear than other portions of the pyramid.

14. The system of claim 11, further comprising a battery electrically coupled to the controller circuit and housed within the enclosure.

15. The system of claim 11, wherein the enclosure further comprises:

a first portion configured to engage with a backside of the ear; and a second portion configured to engage with a frontside of the ear.

16. The system of claim 15, wherein the second portion includes a plug adapted to be inserted into a cavum concha of the ear.

17. The system of claim 16, wherein a position of the plug is adjustable in a direction between a top point of the ear and an anterior notch of the ear.

18. The system of claim 11, wherein the antenna is adjustably coupled to the enclosure to allow for adjustment of a position of the antenna with respect to the enclosure.

19. The system of claim 11, wherein the antenna is coupled to the enclosure and positioned such that when the enclosure is mounted on the ear of the patient the antenna is located above the ear of the patient.

20. The system of claim 11, wherein the antenna includes a dipole or a bowtie configuration.

* * * * *